United States Patent
Mayer et al.

(10) Patent No.: US 9,931,165 B2
(45) Date of Patent: Apr. 3, 2018

(54) LIGHT DIFFUSER AND PROCESS FOR PRODUCING THE SAME

(71) Applicant: Woodwelding AG, Stansstad (CH)

(72) Inventors: Jorg Mayer, Niederlenz (CH); Marcel Aeschlimann, Ligerz (CH); Laurent Torriani, Lamboing (CH); Heinrich Walt, Zollikerberg (CH)

(73) Assignee: WOODWELDING AG, Stansstad (CH)

( * ) Notice: Subject to any disclaimer, the term of this patent is extended or adjusted under 35 U.S.C. 154(b) by 606 days.

(21) Appl. No.: 14/048,614

(22) Filed: Oct. 8, 2013

(65) Prior Publication Data

US 2014/0039474 A1 Feb. 6, 2014

Related U.S. Application Data

(60) Division of application No. 12/487,085, filed on Jun. 18, 2009, now Pat. No. 8,568,395, which is a
(Continued)

(30) Foreign Application Priority Data

May 3, 2004 (CH) ........................................ 778/04

(51) Int. Cl.
 A61B 18/18 (2006.01)
 A61B 18/20 (2006.01)
 A61B 18/22 (2006.01)

(52) U.S. Cl.
 CPC ...... *A61B 18/20* (2013.01); *A61B 2018/2261* (2013.01)

(58) Field of Classification Search
 CPC .. A61B 18/20; A61B 18/22; A61B 2018/2261
(Continued)

(56) References Cited

U.S. PATENT DOCUMENTS 5,209,748 A 5/1993 Daikuzono
5,304,228 A 4/1994 Prince
(Continued)

FOREIGN PATENT DOCUMENTS

EP 0594089 4/1994
FR 2782278 3/2000
(Continued)

*Primary Examiner* — John R Downey
(74) *Attorney, Agent, or Firm* — Rankin, Hill & Clark LLP

(57) ABSTRACT

A light diffuser, which is particularly suitable for introducing diffuse light into a tissue, is produced by interpenetration of a diffuser material in a liquid state into a boundary layer of a porous shaping material, by which process a diffuser surface is formed having a surface structure which represents essentially a negative of the pore structure of the shaping material and includes undercut structures induced by a surface tension. The light diffuser is e.g. produced by introducing a diffuser blank including material that is liquefiable through mechanical vibration into the shaping material and simultaneously stimulating it with mechanical vibrations, such that the liquefiable material liquefies at least there where it is in contact with the shaping material and is pressed into the shaping material. An in situ production of the diffuser is particularly advantageous for photodynamic therapy in bone tissue.

21 Claims, 5 Drawing Sheets

Related U.S. Application Data continuation-in-part of application No. 11/568,553, filed as application No. PCT/CH2005/000246 on May 3, 2005, now abandoned.

(58) Field of Classification Search
USPC .................................................... 606/13–17
See application file for complete search history.

(56) References Cited

U.S. PATENT DOCUMENTS

| | | |
|---|---|---|
| 5,431,647 A | 7/1995 | Purcell, Jr. et al. |
| 5,530,780 A | 6/1996 | Ohsawa |
| 5,695,583 A | 12/1997 | van den Bergh et al. |
| 5,741,323 A | 4/1998 | Pathak et al. |
| 5,849,035 A | 12/1998 | Pathak et al. |
| 6,176,871 B1 | 1/2001 | Pathak et al. |
| 6,289,150 B1 | 9/2001 | Zarian et al. |
| 6,364,874 B1 | 4/2002 | Bays |
| 6,417,247 B1 | 7/2002 | Armstrong et al. |
| 7,329,274 B2 | 2/2008 | Altshuler et al. |
| 7,397,983 B2 | 7/2008 | Beyer et al. |
| 2002/0016596 A1 | 2/2002 | Cooper |
| 2002/0094161 A1 | 7/2002 | Maitland |
| 2005/0143732 A1* | 6/2005 | Burch ................... A61N 5/062 606/53 |

FOREIGN PATENT DOCUMENTS

| | | |
|---|---|---|
| WO | 85/03781 | 8/1985 |
| WO | 02/069817 | 9/2002 |
| WO | 03/090866 | 11/2003 |

* cited by examiner

LIGHT DIFFUSER AND PROCESS FOR PRODUCING THE SAME

BACKGROUND OF THE INVENTION

Field of the Invention

The invention concerns a light diffuser according to the generic term of the first independent claim, as well as a method for producing the light diffuser according to the generic term of the corresponding independent claim. The light diffuser according to the invention is suitable for the diffuse deflection of light delivered to the diffuser from a light source or through a light conductor in an essentially axial direction. The light diffuser according to the invention is e.g. suitable for application in endoscopic methods, e.g. for the targeted introduction of diffuse light into tissue structures, in particular into bone tissue, and for the consistent illumination of hollow biological structures.

Description of Related Art

Diffuse light is applied in tissue structures e.g. in the so-called photodynamic therapy methods known in particular for the treatment of tumorigenic diseases. For this purpose a substance, which is sensitive to light and accumulates mainly in the tumorous tissue, is administered to a patient. Then the tumorous tissue is illuminated with light of a specific wavelength, which activates the photosensitive substance and triggers a chemical reaction, which in turn destroys the tumorous cells.

Activating the photosensitive substance by light initiates the destruction of the tumorous cells. It is therefore important to be able to introduce a specific dose of light adjusted to the size of the tumour in a targeted manner and as homogenously as possible into the tumorous tissue, which is usually achieved by means of a light conductor, wherein the distal end of the light conductor is designed as a diffuser. The task of the diffuser is to scatter the light, which propagates essentially axially inside the light conductor, in as many different directions as possible and as evenly as possible. The diffuser is brought to, or introduced into the tissue to be illuminated and is supplied by the light conductor with light of a given wavelength. The diffuser distributes the light introduced by the light conductor as homogenously as possible in a space whose shape is advantageously adapted to the circumstances.

Such diffusers are known to be manufactured by corresponding modification of the distal end of a light conductor and/or by placing an appropriately equipped end-piece on or at the distal end of the light conductor. Thus e.g. the sleeve placed around the light conducting fibre is removed at the distal end of the light conductor and the surface of the light conducting fibre is roughened slightly, etched or treated with suitable tools to create a light scattering surface, as it is disclosed e.g. in the publication FR-2782778. Light scattering end-pieces usually comprise a transparent material filled with particles (e.g. transparent plastics with particles of aluminium oxide or titanium oxide). In case the light scattering effect of the modified fibre surface and/or of the end piece does not suffice to deflect an adequate portion of the supplied light from the axial direction, it is also suggested that a mirror is positioned at the distal end of the light conductor or of the diffuser, reflecting non-deflected light back into the diffuser area (e.g. disclosed in U.S. Pat. No. 5,695,583, US-2002/0094161 and U.S. Pat. No. 5,431,647).

Known light diffusers, thus, essentially represent the distal end of a light conductor and for medical purposes are brought to, or introduced into the tissue to be treated with minimally invasive methods and removed after the treatment. For the treatment, the proximal end of the light conductor is attached to a light source, wherein the light source is e.g. a laser, but can also be the distal end of another light conductor.

The known diffusers described above are manufactured by relatively elaborate methods and are therefore expensive. They nevertheless have to be treated as disposable items as they are difficult to clean and sterilize and the risk of infection is clinically often considered too high for a repeated application. For photodynamic therapy, the diffuser has to be brought into the immediate vicinity of, or even into the tissue to be treated and it has to be retracted from this tissue after the treatment, which is connected with the danger of diseased cells, e.g. metastasizing tumorous cells, being spread.

BRIEF SUMMARY OF THE INVENTION

The object of the invention is to create a light diffuser as well as a method for producing the same. The light diffuser according to the invention is to be suitable for most diverse applications, not only medical but also technical applications, in particular however for the aforementioned introduction of diffuse light into bone tissue (photodynamic therapy) and for the homogenous illumination of hollow biological structures (hollow organs). Compared to the production of known light diffusers, the method for producing the light diffuser according to the invention is to be simpler and it is to enable a simple adjustment to given circumstances, of the geometry of the space to be provided with diffuse light.

This object is achieved by the light diffuser and the method for its production as defined in the claims.

The method according to the invention, serving for producing a light diffuser, or for supplying diffuse light to tissue, in particular to bone tissue respectively, is based on the following finding: When an implant consisting of a thermoplastic material is implanted in bone tissue by means of mechanical oscillation, in particular ultrasound, as described e.g. in the publication WO-02/069817, its surface changes in particular where this surface is, or is brought into contact with the bone tissue, and in particular when such locations are provided with energy directors. At these points the thermoplastic material liquefies and is pressed into uneven patches and pores (trabecular chambers) of the bone tissue; it interpenetrates the bone tissue. Under normal implantation conditions this interpenetration e.g. in spongeous bone tissue reaches a depth equivalent to about two trabecular chambers. After re-solidification of the thermoplastic material, this material and the bone tissue are connected to each other in a positive fit connection, which is e.g. exploited as a primary stabilisation of the implant immediately after the implantation.

It is found that the thermoplastic material penetrating the bone tissue also lends the implant a surface structure ideally suited to scatter light, which is coupled into a proximal face of a transparent implant in axial direction, from the implant into the bone tissue surrounding the implant. In its implanted condition the implant represents an excellent light diffuser. Prior to the implantation, it is a kind of diffuser blank.

The change to the surface caused by the implantation in bone tissue by mechanical vibration, by which a corresponding implant (diffuser blank) becomes a diffuser, develops in the liquid condition of the diffuser material, so that the emerging structures have forms created in a flowing motion, therefore induced by a surface tension, and essentially representing a negative of the porous bone structure, i.e. in particular comprising undercuts.

When a laser beam of a 625 nm wavelength is coupled from a light conductor (diameter 0.4 mm) to the proximal face of a pin-shaped implant of poly-LDL-lactide (length 25 mm, diameter 3.5 mm), ca. 75% of the coupled light intensity is measured at the distal end of the implant, which represents a very anisotrope light distribution. If the same implant is driven into "sawbone" (closed pore polyurethane foam reinforced by glass fibre), whose structure closely resembles bone, by ultrasound and without prior drilling, the implant surface changes and becomes light scattering. In this state of the implant, an essentially equal light intensity is measured (distal end: 0.22 W/mm2; circumferential surface: 0.20 W/mm2) across the implant surface where altered by the implantation. These measurements show that the altered surface scatters the coupled light very homogenously, i.e. turns the implant into a very good light diffuser.

The finding described above does not only apply to bone tissue but can be transferred to other porous materials, in particular to artificial materials, wherein such artificial shaping materials are to comprise a porous structure like bone tissue. The pores of such shaping material are advantageously sized between 0.005 and 1.0 mm. The properties of the shaping material furthermore must be such that its porous structure can offer sufficient resistance for enabling liquefaction and interpenetration of the thermoplastic material of the diffuser blank when the diffuser blank is introduced in the shaping material by mechanical vibration. If this is not the case, the porous structure collapses and the interpenetration of the porous shaping material necessary for the development of the desired surface structure does not take place.

Instead of liquefying, by mechanical vibration, a solid diffuser blank material in areas where the diffuser blank is in contact with the porous shaping material, it is also possible to liquefy the diffuser blank material in other ways, e.g. by absorption of electromagnetic radiation (e.g. laser light) at least in the surface regions of the diffuser blank. In both cases, the liquefied material is pressed into the porous shaping material through pressure applied to the diffuser blank. Furthermore, it is possible to press or suck a liquid diffuser material into the porous shaping material (e.g. by capillary action or pressure difference). The liquid diffuser material is then hardened by cooling (e.g. thermoplastic polymers, glasses), by a suitable chemical reaction (e.g. cross-linking resins such as epoxy resin or silicone) or by thickening (e.g. gels or hydrogels on the basis of polyethylene glycols, alginates, chitosanes, collagens and their copolymers or blends). This method not only gives a greater choice of diffuser design than the "implantation method", but it also makes it possible to create a gel-like, i.e. flexible diffuser in a flexible shaping material, which is then not removed from the diffuser and which is suitable e.g. for illumination of the walls of hollow spaces, as it can adapt to diverse shapes of hollow spaces, or e.g. can even be left in a corresponding space if a resorbable hydrogel is used. Such a light diffuser can e.g. in the case of tumour excision wounds not only assume the function of illumination but also the function of wound tamponing after irradiation, to which purpose it is advantageously modified in a known manner with active substances such as cytotoxins, anti-inflammatory substances, antibiotics or growth factors for the further treatment of the defect.

The properties of an artificial porous shaping material suitable for producing the diffuser according to the invention can be such that it can be removed from the diffuser produced therein e.g. by dissolution in an appropriate solvent, by etching, by melting or subliming. Providing that the shaping material has at least locally suitable properties, it can also remain on the diffuser surface and form a kind of diffuser cap, which, due to its porosity, can e.g. further scatter light deflected by the diffuser. Such a diffuser cap of the porous shaping material may already have the shape of a cap, i.e. relatively thin walls, when the diffuser is produced, or it may be appropriately processed afterwards. The diffuser cap can also be fashioned for a specific non-optical additional function or can be shaped appropriately by a subsequent addition or removal of material or by re-forming. The porosity of the shaping material can be homogenous. In particular if the diffuser cap has specific non-optical additional functions, it may be advantageous to fashion the porosity inhomogeneous and to vary it depending on the function of each part of the diffuser cap. Thus a diffuser cap can be porous where it is to be interpenetrated by a diffuser material while the exterior surface of the cap is smooth and free from pores in order to minimize friction in the tissue and contamination e.g. in the endoscopic application.

Diffusers according to the invention, produced by means of an artificial shaping material, suit non-medical and medical applications, but in particular the introduction of diffuse light in soft tissue or in tissue voids (e.g. blood vessels, respiratory passages or digestive tract). In that case, the same procedure is followed for the introduction of the diffuse light as with diffusers according to the state of the art, wherein the diffuser according to the invention is coupled with a light conductor or a light source and is positioned for the application. Then light of a desired wavelength is coupled from the light conductor into the diffuser, which scatters the light and, thus, brings it into the tissue. A particular advantage of flexible diffusers produced by the above mentioned method is the fact that due to its flexibility, the diffuser can be bent by the operator using per se known catheter techniques around a large solid angle, such enabling a corresponding control of the instrument on one hand and a targeted illumination on the other.

It is also possible to couple light to be scattered only into a part of the diffuser and to equip other areas thereof for other functions, wherein these other areas are e.g. not transparent.

The use of viable tissue, in particular of bone tissue, as porous shaping material for producing the diffuser from a diffuser blank means that the diffuser blank is implanted and the light scattering surface structures develop during implantation (in situ). It is not imperative to create an opening (e.g. a bore) in the osseous material prior to the implantation. E.g. the cortical layer of a bone can be drilled in advance and the implant positioned in the bore before it is driven by pressure force and simultaneous vibration into the spongiosa, without drilling the latter. With such a diffuser produced in situ, a tumour (or metastasis) located in the spongiosa can be illuminated in the simplest way. The diffuser implant can remain in the bone tissue for further illuminations, where with its intensive anchoring it may represent a welcome further reinforcement of the osseous tissue debilitated by the tumour. The diffuser implant can also consist of a biologically resorbable light conducting material so that it does not need to be removed after its use for the illumination of the tissue and is gradually replaced by regenerated bone tissue.

If the diffuser implant is to remain in the place of implantation after the illumination, care must be taken that the proximal end of the diffuser implant does not protrude substantially from the bone and that its proximal end is primed for the connection with a light conductor which is advanced to this proximal end for the illumination as in known endoscopic methods.

The crucial advantage of the diffuser produced by implantation in viable bone tissue over known diffusers used for the same purpose, is the fact that precursory drilling is not necessarily needed and that the implant does not necessarily need to be removed, or to be removed immediately after the application of the diffuser for an illumination or activation. This means that no element needs to be removed from the tissue to be treated before or immediately after the treatment and therefore the danger of spreading diseased cells, e.g. metastasizing tumorous cells is considerably reduced.

BRIEF DESCRIPTION OF THE DRAWINGS

The diffuser according to the invention and the method for its production are described in detail in connection with the following Figs., wherein.

DETAILED DESCRIPTION OF THE INVENTION

Figure 1:
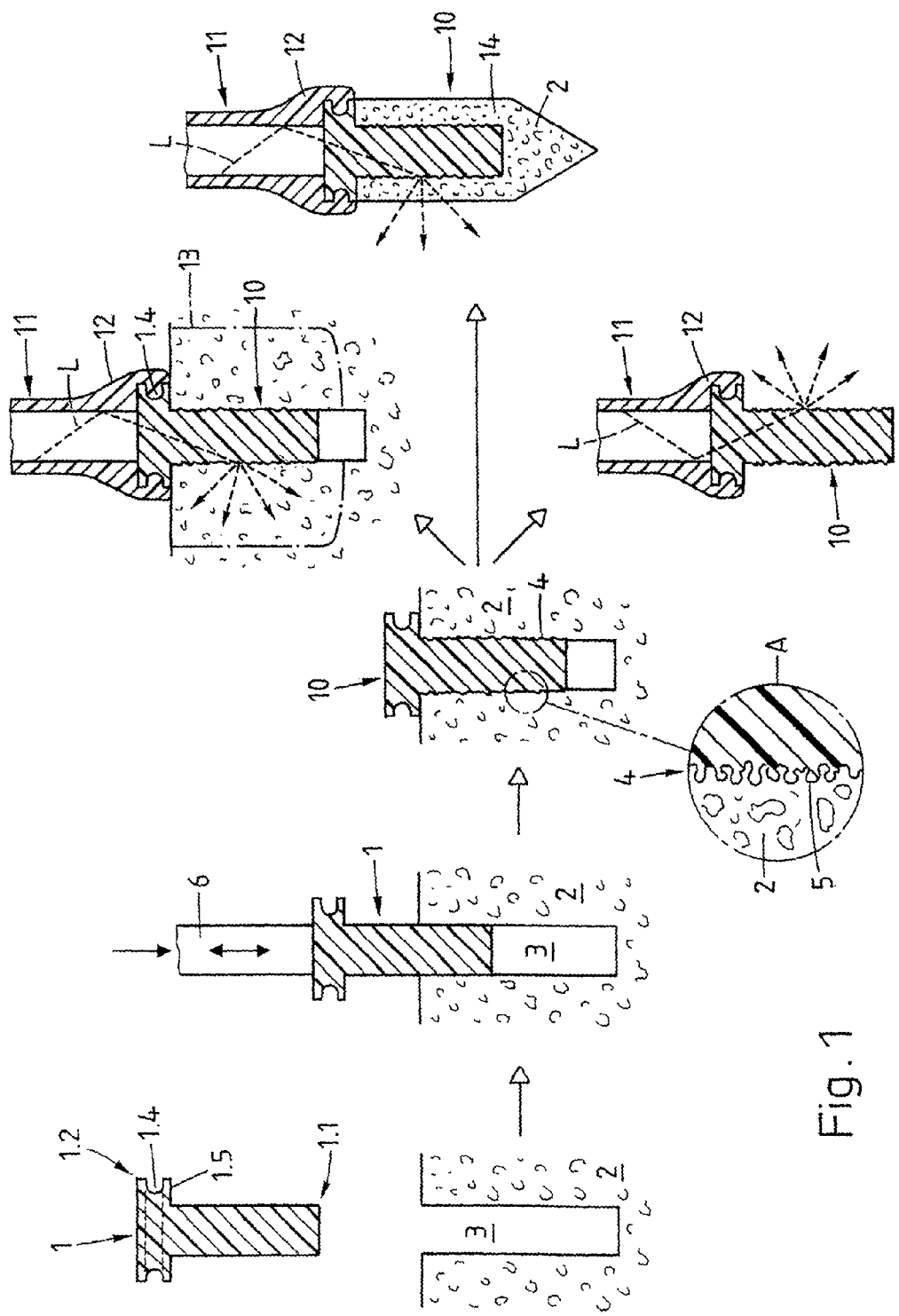
FIG. 1 shows the method for producing the light diffuser according to the invention on the example of a diffuser, which is to have a more-or-less cylindrical active range.

FIG. 1 illustrates the method according to the invention for producing a light diffuser with the aid of a sequence of sections through the diffuser during production. It shows the production of an exemplary light diffuser, which is to have a more-or-less cylindrical active range. As described above, the diffuser can be produced in situ in a bone, or ex situ by means of an artificial shaping material, which is interpenetrated by the diffuser material in a contact layer, wherein for using the diffuser, the shaping material may be left as a diffuser cap on the diffuser or is removed therefrom.

The diffuser blank 1 consisting of a suitably transparent thermoplastic material (in a solid state) has e.g. an essentially cylindrical form with a distal end 1.1 and a proximal end 1.2, wherein the proximal end 1.2 is furnished with a means to couple an appropriately primed distal light conductor end 11, e.g. with a circumferential groove 1.4.

In the illustrated example, essentially the whole circumferential surface of the diffuser blank 1, though not its distal face, is to be structured for the light scattering function. The surface to be structured, thus, consists of the thermoplastic material and may be additionally equipped with energy directors, e.g. with a pattern of humps or with axially extending ribs (not shown). The surfaces of the diffuser blank 1, which are not to be structured for a light scattering function, are advantageously polished, in particular the proximal face into which the light is to be coupled and the distal face which is to reflect light not scattered from the diffuser. On its distal face, the diffuser blank 1 may also comprise an appropriate mirror-like coating.

For producing the light diffuser 10 from the diffuser blank 1, an opening 3 (e.g. a bore) is provided in a porous shaping material 2, the opening being dimensioned, thus that the diffuser blank 1 is at least locally slightly larger than the dimensions of the opening. The length of the bore is greater than the axial length of that part of the diffuser blank 1 to be positioned in the bore. To prevent the diffuser blank from being brought too far into the bore, the blank comprises appropriate means, e.g. a proximal collar 1.5.

The diffuser blank 1 is positioned in the bore 3 of the porous shaping material 2 and then pressed into the bore 3, e.g. by means of a sonotrode 6 excited by ultrasonic oscillation. The thermoplastic material of the diffuser blank liquefies where it is in contact with the porous shaping material 2, and in particular where energy directors (not shown) of the thermoplastic material are in contact with the porous shaping material 2, which excited by the mechanical vibration causes stress concentrations in the diffuser material. The liquefied diffuser material is pressed into the pores of the porous shaping material 2 and interpenetrates the porous shaping material in a boundary layer 4, advantageously comprising a thickness of ca. 0.02 to 1.0 mm. Therein, the light scattering surface structure 5 is formed on re-solidification of the diffuser material, as illustrated in detail A, and therewith the diffuser blank 1 becomes a diffuser 10. The produced surface structure 4 corresponds essentially with the pore structure of the porous shaping material 2 or a cast negative thereof respectively, i.e. it comprises forms that are undercut, and, because they were formed in the liquid state of the diffuser material, induced by a surface tension.

As illustrated on the right hand side of FIG. 1, for its use, the diffuser 10 is supplied with light L by coupling a distal light conductor end 11 to its proximal end, e.g. by securing an appropriate coupling piece 12 in the groove 1.4. Such couplings are part of the state-of-the-art technology and are therefore not further described here.

The diffuser 10 can remain in the porous shaping material 2 for its illuminative function and serve for introducing diffuse light into this shaping material, e.g. as an illuminative implant in bone tissue, as illustrated at the top right in FIG. 1. The diffuser scatters the light in a very homogenous manner in a fairly cylindrical active area, as indicated by the chain line 13 (see also FIG. 3).

The porous shaping material 2 (in this case inevitably transparent) can, on the other hand, also form a diffuser cap 14 (FIG. 1, centre right). Such a diffuser cap protects the diffuser and can also be primed e.g. for an additional scattering of the light it receives from the diffuser 10 or for further, non-optical functions. The diffuser cap may furthermore be primed for further light conducting, distracting, screening, focussing or filtering functions, as known from the state of the art. In addition to its optical functions the diffuser cap, if need be appropriately finished, can represent an instrument or part of an instrument (see FIGS. 11 and 12).

The porous shaping material 2 may be removed from the diffuser 10 so that the light scattering surface structure 4 is the only light scattering means of the diffuser 10 (FIG. 1, bottom right).

For the embodiment of the method according to the invention according to FIG. 1, the diffuser material is selected with regard to the diffuser blank 1, i.e. comprising sufficient mechanical stability to be pressed into the bore 3. For being as energy-efficient as possible, which, in particular for an in situ production in viable bone tissue, is also protective, the diffuser material is selected for damping the mechanical vibration as little as possible (elasticity module greater than 0.5 GPa).

Transparent or sufficiently transparently processed thermoplastic diffuser materials suitable for diffuser blanks to be implanted in bone tissue are e.g. the biologically resorbable polymers based on lactic and/or glycolic acid (PLA, PLLA, PGA, PLGA etc), in particular poly-LDL-lactide (e.g. available from Böhringer under the trade name Resomer LR708) or poly-DL-lactic acid (e.g. available from Böhringer under the trade name Resomer R208) or the likewise resorbable polyhydroxyalkanoates (PHA), polycaprolactones (PCL), polysaccharides, polydioxanons (PD), polyanhydrides, polypeptides or corresponding copolymers or the non-resorbable polyolefines (e.g. polyethylene), polyacrylates, polymethacrylates, polycarbonates, polyamides, polyesters, polyurethanes, polysulphones, polyphenylsulphides, liquid-crystal-polymers (LCPs), polyacetals, halogenated polymers, in particular halogenated polyolefines, polyphenylsulphides, polysulphones, polyether or corresponding copolymers and polymer mixtures.

The porous shaping material 2 is selected with regard to its pore structure remaining stable when in contact with the liquefied diffuser material but being interpenetrable by this material. An artificial porous shaping material comprises for the interpenetration suitable porosity, wherein this may be open porosity or closed porosity with partitions perforable under the circumstances of the method. The pores are advantageously sized between 0.01 and 1.0 mm. Sizes and distribution of the pores may also comprise gradients e.g. for the generation of fractal surface geometries or for the production of diffuser caps with a smooth pore-free surface.

Examples of artificial porous shaping materials to remain as diffuser caps on the diffuser and to assume further functions are e.g. glasses (sintered glass, foam glass), amorphous ceramics or ceramics with a high content of glass phases (oxidized ceramics such as e.g. aluminium oxide or titanium oxide or non-oxidized ceramics such as e.g. nitrides), doted ceramics (e.g. for further optical-physical functions such as e.g. filtering or stimulation of fluorescence) or amorphous or partly amorphous thermoplastic or cross-linked polymers. For producing porous forms of said materials, per se known methods are used such as e.g. foaming methods, vacuum-methods, leaching methods, sintering methods or segregation methods.

If the porous shaping material is to be removed from the diffuser after its production, it has a lower melting point than the diffuser material and is removed by heat or it is soluble in a solvent in which the diffuser material is not soluble and is removed by means of a solvent. Further suitable removing methods are etching procedures or sublimation or evaporation techniques. Thus e.g. foamed gypsum used as porous shaping material can be removed from a diffuser of an amorphous polymer by means of a moderate acid (solvent) or a glass with a high content of sodium (e.g. waterglass) can be removed with water. If the porous shaping material is to be removed from the finished diffuser it may be equipped for further functions not compatible with the diffuser function. The shaping material may e.g. comprise a substance capable of absorbing electromagnetic radiation (e.g. laser light of a predetermined wavelength range, e.g. visible or infrared light) at least in the area near the distal end of the diffuser blank. By coupling corresponding radiation into the transparent diffuser blank material, transmitting it through the diffuser blank material and absorbing it in the shaping material, heat is produced and the diffuser blank material is liquefied by this heat in addition to or instead of the heat produced by the mechanical vibration.

The diffuser blanks and the diffusers shown in FIG. 1 are of a cylindrical shape. Of course this is not a condition for the invention. Similarly, diffuser blanks and diffusers may comprise any chosen cross section and may e.g. taper towards the distal end either continuously or in steps.

Figure 2:
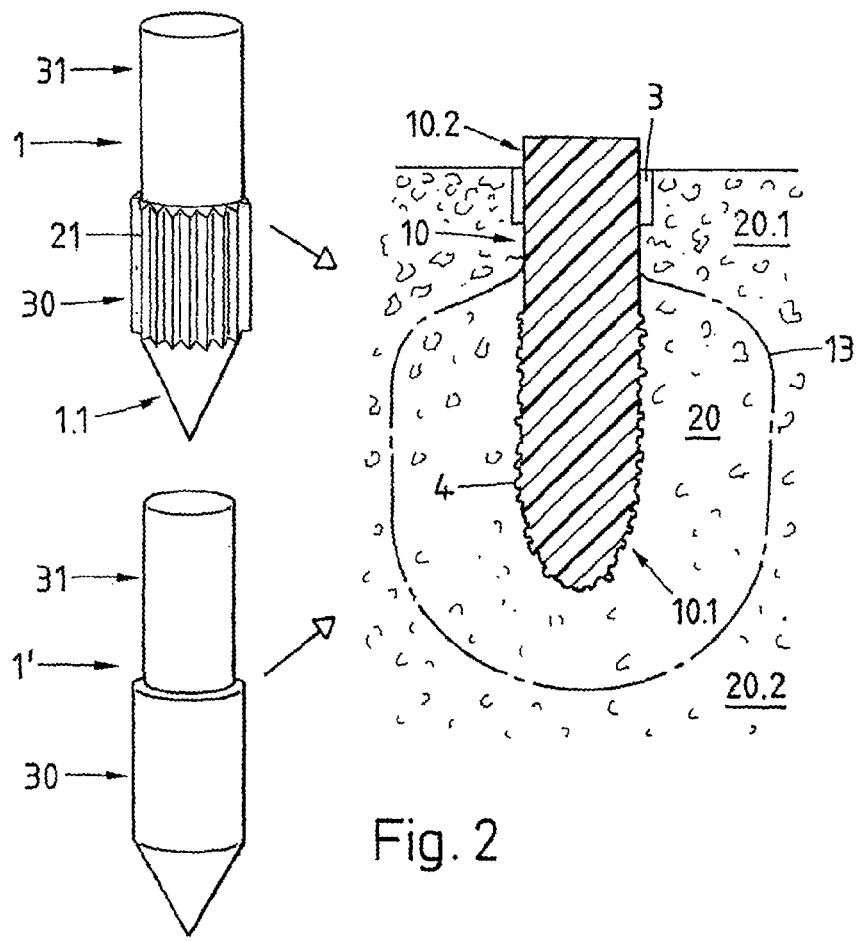
FIG. 2 shows a further exemplary diffuser blank and the light diffuser according to the invention produced therefrom, which diffuser comprises a more ball-shaped active range.

FIG. 2 shows a further diffuser blank 1 and the light diffuser 10 produced thereof e.g. in situ in a bone 20 (porous shaping material). The diffuser blank 1 according to FIG. 2 has a distal end 1.1 which is pointed, and only a distal region 30 of its circumferential surface is provided with protruding energy directors 21 (e.g. axially extending ribs) for producing the light scattering surface structure 4. The proximal region 31 of the circumferential surface is e.g. polished or comprises a mirror-like coating.

For the implantation of the diffuser blank 1, a corresponding opening 3 is provided e.g. in the cortical layer 20.1 of the bone 20, which opening is advantageously slightly larger than the cross-section of the diffuser blank. The diffuser blank 1 is then positioned in the opening with its distal end 1.1 facing forward. The pointed distal end 1.1 of the diffuser blank 1 is then driven into the cancellous bone 20.2 by means of pressure and mechanical vibration, and the diffuser material is liquefied in the region of the distal end 1.1 and of the circumferential surface 30 and is pressed into the porous structure of the spongiosa. Thereby, a diffuser 10 with a distal diffuser part 10.1 and a proximal light conductor part 10.2 is formed.

Obviously, the depth of the diffuser part in the bone is predetermined by the axial length of the diffuser blank 1 and the axial length of the circumferential surface region 31 not furnished with energy directors. The shape of the active region of the diffuser 10 according to FIG. 2 is spherical or spherical/cylindrical (chain line 13) depending on the axial length of the surface region 30 furnished with energy directors 21.

Due to its proximal light conducting part, the diffuser blank 1 according to FIG. 2 is suitable in particular as an illuminative implant for the photodynamic treatment of tumours or metastases inside the bone. Therein, the length of the diffuser blank 1 is adjusted to the depth of the bone area to be treated, and the length of the surface range 30 furnished with energy directors 21 to the size of the bone area to be treated. The diffuser blank 1 is driven from the bone surface into the bone until its distal end is positioned in the bone area to be treated and the diffuser blank has, thus, become a diffuser. Then, a distal light conductor end or a light source is attached to the proximal end of the diffuser and the bone area to be treated is illuminated.

Obviously, for the illumination, there is no need to open up the bone area to be treated and to bring it into contact with any tool, which relevantly reduces the danger of diseased cells spreading from this area compared to illumination methods according to the state-of-the-art technology.

Depending on the diffuser material, it may be adequate not to furnish the distal area (surface range 30) of a diffuser blank 1' (in FIG. 2 illustrated below the diffuser blank 1) with energy directors 21 but to give it a slightly larger cross-section than the proximal surface range 31, so that the surface of the distal range 30 protrudes slightly from the surface of the proximal range 31 and, thus, comes into more intensive contact with the bone tissue 20 in a bore 3 than the further surface ranges 31, in which no light scattering surface structure is to be generated.

As already described in connection with FIG. 1, it is of course also possible for the embodiment of the method according to FIG. 2 to use an artificial shaping material and to either leave it on the diffuser as a diffuser cap or to remove it therefrom. The method according to FIG. 2 is particularly suitable for the use of a liquid diffuser material. The liquid diffuser material is pressed or sucked (pressure reduction on the outside of the form) into a mold, wherein the mold consists of the porous shaping material or comprises an interior coating of the porous shaping material. The diffuser material interpenetrates the porous shaping material in the range of a boundary layer. The liquid diffuser material within the form and the named boundary layer is then hardened through e.g. cooling, polymerisation or thickening, thus producing a light diffuser according to the invention, which is further used in the manner described above.

As castable diffuser materials, cross-linkable polymers (e.g. cross-linked chemically, thermally or by radiation), such as e.g. silicones, polyurethanes, epoxy resins or polyester resins can be used. Likewise suitable are thermoplastic polymers, gels (e.g. PEG, PHEMA, acrylates, saccharides, alginates, chitosanes, or copolymers and mixtures of alginates and chitosanes), glasses, glass ceramics or oxidic and non-oxidic ceramics with a high content of amorphous phase. The castable material as well as a solid diffuser material may further comprise at least one of per se known scattering materials such as titanium oxide, mica, calcium phosphates, sodium phosphates, calcium carbonates, saturated fatty acids, polysaccharides, glucose etc. Depending on the wavelength of the incident electromagnetic radiation such materials may selectively serve as scattering or absorbing agents. This means that for production of a diffuser according to the invention from a solid diffuser blank material containing the named agent(s), corresponding radiation can be coupled into the diffuser blank for producing heat (instead of or in addition to the heat produced through the mechanical vibration) for liquefying the diffuser blank material.

As a removable porous shaping material for producing a diffuser from a gelling diffuser material e.g. a Wood's alloy can be used. Such alloys can be sintered at very low temperatures and after the production of the diffuser they can be removed from the gel at temperatures just a little above ambient temperature. Alternatively, the diffuser can be removed from the mold by removing the solvent in the gel, i.e. by drying the gel, which reduces its volume.

Figure 3:
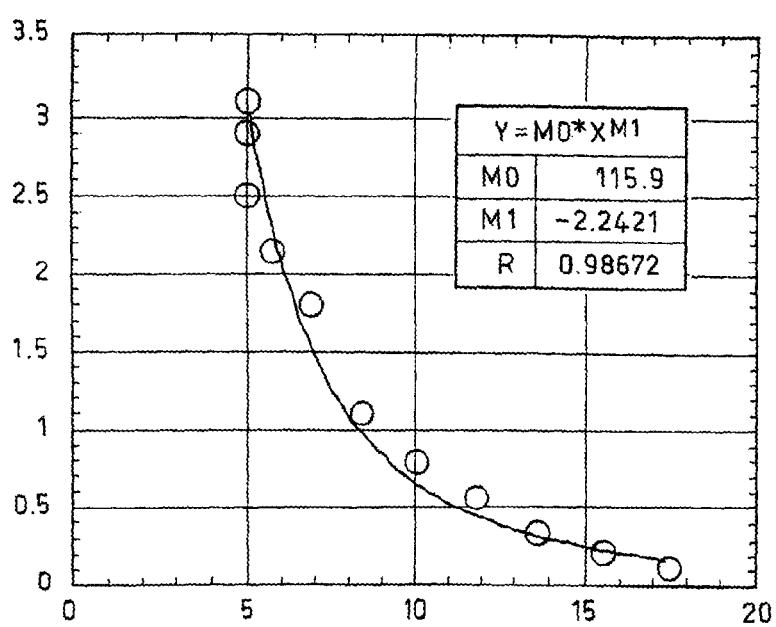
FIGS. 3 and 4 show intensity profiles of the light diffusers according to FIGS. 1 and 2.

FIG. 3 shows an intensity profile measured for a diffuser according to FIG. 1. The diffuser was produced by implanting a pin-shaped diffuser blank (length 25 mm, diameter 3.5 mm) of poly-LDL-lactic acid by means of ultrasound (Branson hand tool, 20 kHZ) in an appropriately predrilled spongeous bone (femur of a sheep). The depth of the bore exceeded 12 mm and the implant was driven into a depth of 12 mm, i.e. not to the bottom of the bore. Then laser light of 625 nm wavelength (power 0.5 W) was coupled into the implant via a light conducting fibre (diameter 400 µm) through the proximal face and the light intensity was measured by means of a silicone detector (diameter 7.9 mm) at various points of the bone.

The diagram shown in FIG. 3 shows the measured light intensity [mW] versus the distance from the diffuser surface [mm]. The fit with an exponentially descending curve results in an exponent of circa—−2.2, which suggests a space illuminated by the diffuser with a more cylindrical (theoretical exponent=−2) than spherical (theoretical exponent=−3) form.

The measured light intensities show, that it is possible to supply a bone volume of ca. 1.5 cm diameter with an energy of 10 J, which is sufficient for a cytotoxic photodynamic therapy treatment, with the aid of an implant of 3.5 mm diameter and a ca. 15 min. radiation time.

Figure 4:
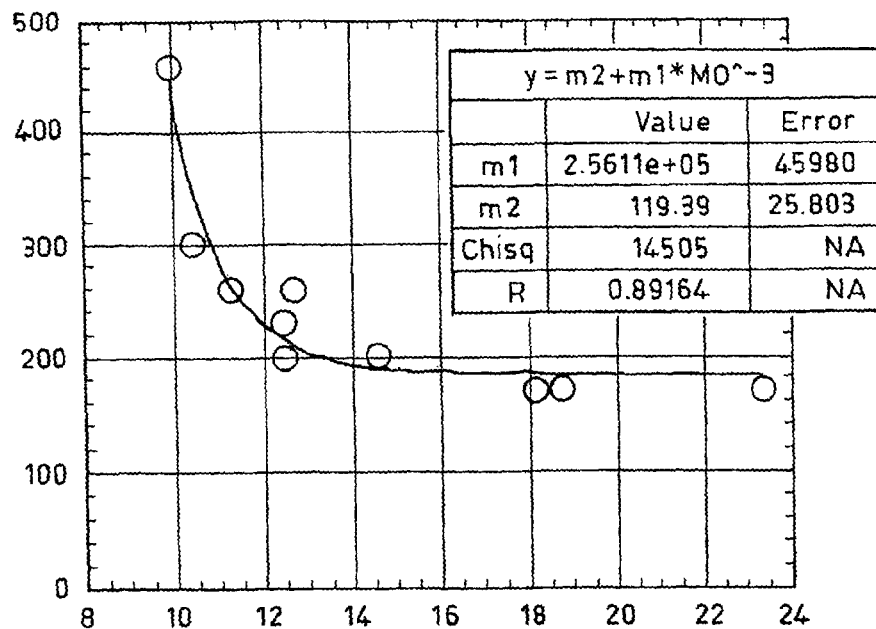

FIG. 4 shows an intensity profile measured on a diffuser according to FIG. 2. The diffuser was produced by pressing a pin-shaped diffuser blank (length 25 mm, diameter 3.5 mm) of poly-LDL-lactic acid using ultrasound (Branson hand tool, 20 kHZ) without pre-drilling into a piece of "sawbone" (glass fibre reinforced polyurethane foam) to a depth of 12 mm. Then, laser light of 625 nm wavelength (power 0.5 µW) was coupled from a light conducting fibre (diameter 400 µm) through the proximal face into the implant and the light intensity was measured by means of a fibre-detector (diameter 200 µm) at various points in the piece of sawbone.

The diagram shown in FIG. 4 shows the measured light intensity [counts] versus the distance from the diffuser surface [mm]. The fit with an exponentially descending curve with an exponent of −3 is good (r=0.89) and indicates an essentially spherical form of the space illuminated by the diffuser.

Figures 5, 6:
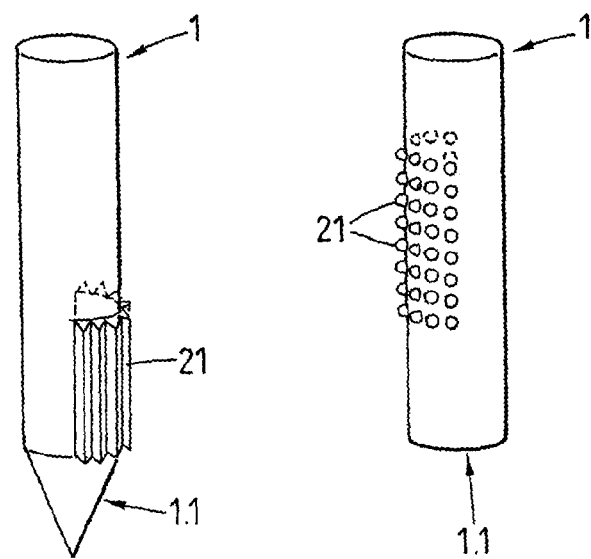
FIGS. 5 and 6 show further exemplary embodiments of diffuser blanks suitable for producing light diffusers with various active ranges.

FIGS. 5 and 6 show two further exemplary diffuser blanks 1, from which diffusers for various applications can be produced by the method according to the invention. The diffuser blank 1 according to FIG. 5 comprises a pointed distal end 1.1 and the distal region of its circumferential surface is furnished with energy directors 21 (e.g. axially extending ribs) around half the circumference, so that a light scattering structure can be generated only in this surface range. Such a diffuser blank results in a diffuser with an active area comprising roughly the shape of a hemisphere. The diffuser blank 1 according to FIG. 6 comprises a blunt distal end 1.1 and a middle region of its circumferential surface is furnished with energy directors 21 (e.g. humps) halfway around the circumference. Using the method illustrated in FIG. 1, this diffuser blank produces a diffuser with an active area roughly equivalent to half a circular cylinder.

Diffusers with active areas of most diverse shapes can be designed from diffuser blanks like those illustrated in the FIGS. 5 and 6. Therein the diffuser blanks do not necessarily need to be pin-shaped and to comprise circular cross-sections as illustrated. They can also have a more compact form, be conically shaped and/or comprise polygon or irregular cross-sections.

Figure 7:
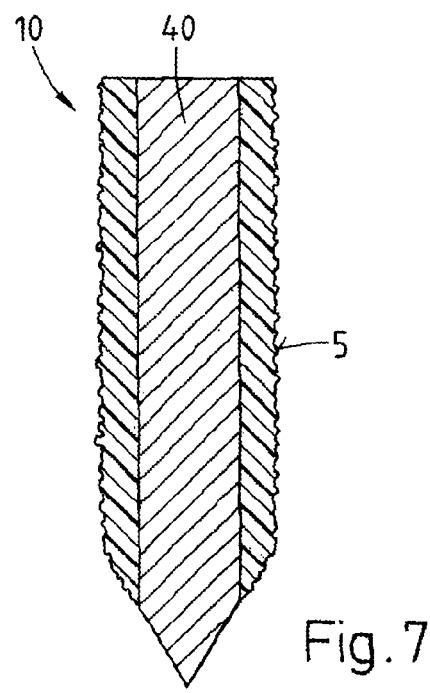
FIG. 7 shows a further light diffuser according to the invention comprising a diffuser core primed for additional functions.

FIG. 7 is an axial section of another diffuser 10 according to the invention comprising a diffuser core 40, wherein the diffuser core 40 is equipped for further, e.g. non-optical functions. The diffuser material (e.g. polymerpine) bearing the light scattering surface structure is arranged on the diffuser core 40 periphery and covers the surface of the diffuser core 40 completely or partially. The diffuser core 40 consists e.g. of titanium and in a diffuser implant assumes e.g. a load bearing function. The diffuser can be produced in situ or ex situ from a corresponding diffuser blank.

Figure 8:
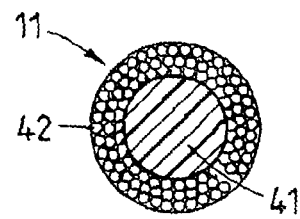
FIGS. 8 and 9 show various ways of coupling light into a light diffuser according to FIG. 7.

Light is to be coupled into the diffuser 10 according to FIG. 7, only through a part of the proximal face (outer ring). To this end e.g. a light conductor 11 is used as illustrated in cross-section in FIG. 8. This light conductor 11 comprises a conductor core 41 and light conducting fibres 42 arranged around it, wherein the cross-section of the conductor core 41 is adjusted to the proximal face of the diffuser core 40.

The diffuser core 40 can assume further functions instead of, or in addition to the already mentioned load bearing function and for such purposes consist of an appropriate material. If the diffuser is produced ex situ, such an additional function serves e.g. for controlling the movement of the diffuser on positioning it at a location to be illuminated. If the diffuser or the diffuser cap is fashioned as an instrument (see FIGS. 11 and 12), the additional function can further be a rinsing or suction function for which the diffuser core is designed as a hollow conduct. Further light conductors may extend into such a hollow conduct of a diffuser produced e.g. in situ, wherein the further light conductors have e.g. a recording function and are connected to a micro-camera, which may serve e.g. the simultaneous analysis of an illumination effect or to detect and locate tumorous cells marked by fluorescence.

The diffuser core 40 of a diffuser produced in situ (diffuser implant) may also have a release function in order to administer a drug to the tissue surrounding the diffuser. If resorbable polymers or gels are used as diffuser material, this release function can also be performed directly via the diffuser material. The diffuser core can also be fashioned as an optical element separated from the diffuser and designed for the coupling of light of another wavelength (e.g. in order to activate another photosensitive drug) or for the coupling of infra-red light in order to warm the tissue surrounding the diffuser. The arrangement of the diffuser material on the diffuser core 40 is to be adapted to the function of the diffuser core 40.

Figure 9:
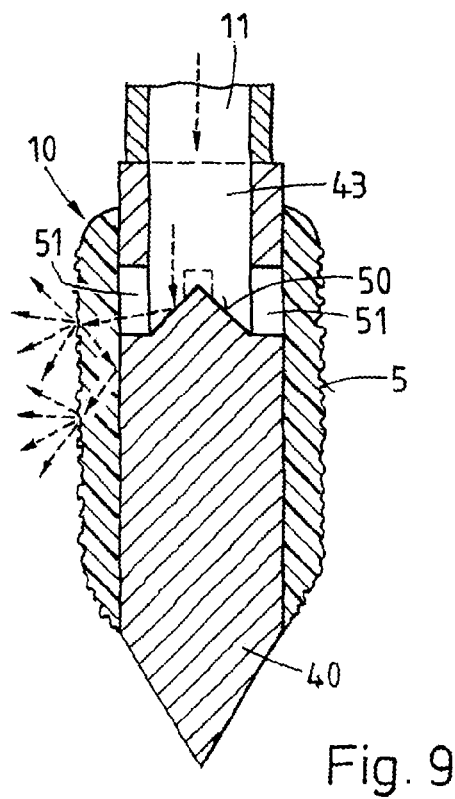

FIG. 9 is an axial section through a further diffuser according to the invention, which can be produced in situ or ex situ and which comprises a diffuser core 40, upon which the diffuser material is arranged e.g. as a coating. For being coupled to the light conductor 11, the diffuser core 40 comprises a proximal region with a central opening 43, wherein e.g. at the bottom of the opening a conical mirror surface 50 is arranged and light emission apertures 51 are arranged above the mirror surface. A distal end of a light conductor 11 (without cladding and with its front face advantageously adapted to the mirror surface 50) is introduced into this opening for coupling light into the central opening 43. The light introduced by the light conductor 11 is reflected from the mirror surface 50 and reaches the diffuser material through the light emission apertures 51, as indicated in FIG. 9 by arrows.

Figure 10:
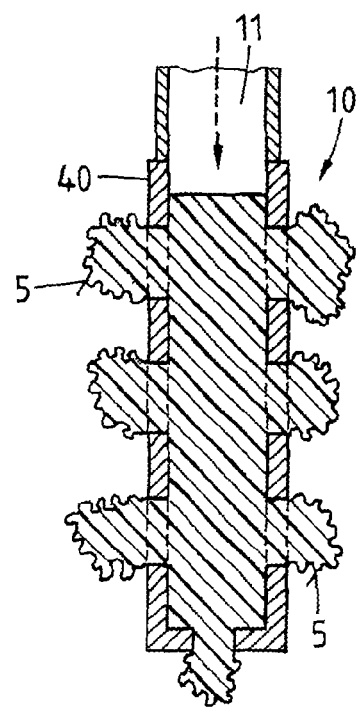
FIG. 10 shows a further light diffuser according to the invention with a hollow diffuser core primed for further functions.

FIG. 10 is an axial section through a further diffuser 10 according to the invention with a diffuser core 40, which diffuser too can be produced either in situ or ex situ. The diffuser core 40 is sheath-shaped and comprises through openings. The diffuser material, e.g. a thermoplastic polymer, gel or thermosetting polymer, is provided in the diffuser blank inside the sheath-shaped diffuser core 40. The diffuser 10 is produced by the diffuser material being pressed with the aid of mechanical vibrations deeper into the diffuser core, through the openings and into the surrounding bone tissue or artificial porous shaping material, and thereby gains the light scattering surface structure 5.

Figure 11:
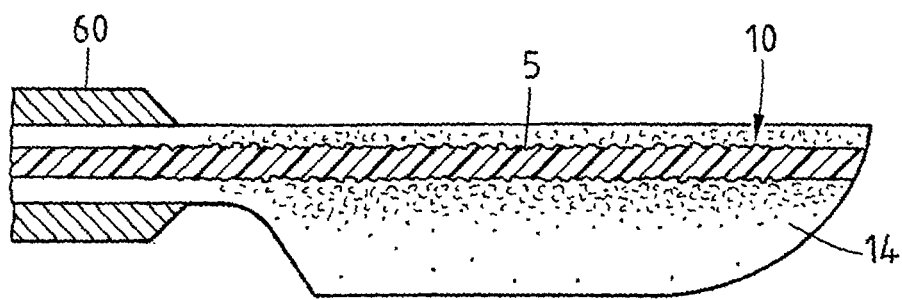
FIGS. 11 and 12 show diffusers according to the invention with diffuser caps primed for further functions.
Figure 12:
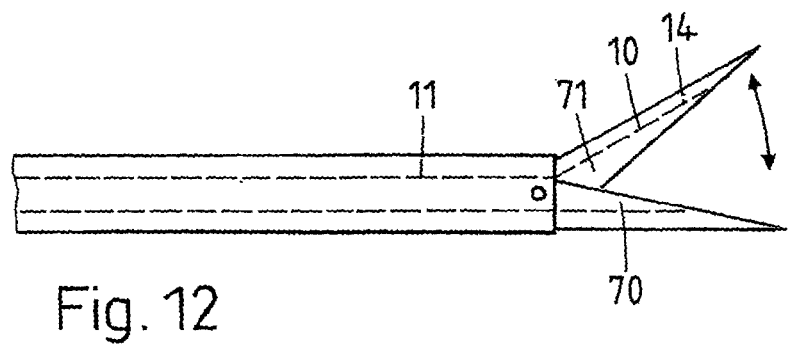

FIGS. 11 and 12 show diffusers 10 according to the invention, which are produced ex situ and comprise a diffuser cap 14 constituting an instrument or a part of an instrument. The instrument illustrated in FIG. 11 is a scalpel shown in axial section, whose blade is the diffuser cap 12, i.e. contains a diffuser 10 according to the invention. The diffuser cap consists e.g. of a transparent ceramic material, which is advantageously only relevantly porous in those areas where it is to serve as a porous shaping material, while it is, in particular in the area of the cutting edge, as compact as possible. A coupling point for a light conductor (not shown) is situated in the region of the handle 60. Due to the coupling of light into the diffuser 10, the scalpel blade becomes luminous and can illuminate homogenously its own working area.

The scalpel blade according to FIG. 11 is produced e.g. by a liquid diffuser material being sucked into an appropriate bore in the blade or being introduced by any of the other aforementioned methods. The blade can be further adapted after the diffuser 10 has been produced. To prevent the diffuser material from gaining a light scattering surface in the region of the handle 60, no porous shaping material, but a compact shaping material is to be provided there.

It is also possible however, to provide a slightly larger bore in the region of the handle 60 than in the region of the blade and to introduce the diffuser material in the shape of a pin into the handle and to press it further into the blade with ultrasound and to transfer the light via the handle functioning as a light conductor into the blade.

FIG. 12 shows, as a further example of a diffuser 10 according to the invention with a diffuser cap 14, an instrument similar to a pair of scissors or nippers, whose blades or legs 70 and 71 are each equipped with a diffuser (schematically indicated by broken line) in the manner described with regard to the scalpel blade of FIG. 11. When the instrument is in use, the blades or legs 70 and 71 serve simultaneously as a source of diffuse light, which illuminates the working area of the instrument.

Obviously, instruments or parts of an instrument equipped with a diffuser as illustrated in FIGS. 11 and 12 can also be equipped with diffusers as known from the state of the art. In other words, it is not a condition for such instruments, that their diffusers have a light scattering surface, which is induced by surface tension and which comprises undercut forms. Other known light scattering surface structures can be created by casting in non-porous structures or by corresponding machining of a diffuser blank before it is positioned in the diffuser cap.

The described diffusers, which can be produced by the illustrated method from the described diffuser blanks, are used e.g. for photodynamic therapy methods, in particular for the treatment of tumorigenic diseases. For such application, in the method for introducing diffuse light into a tissue region as herein described and claimed, in which method one of the herein described and claimed, in particular pin-shaped diffuser blanks is implanted in the tissue, the tissue in question is e.g. a bone tissue and the bone tissue region to be treated is the region of a bone tumour or a metastasis.

The photodynamic therapy method thus comprises the steps of: introducing a photosensitive substance into the tumorous tissue or the metastasis, producing a diffuser according to one of the embodiments of the method here described and claimed (in situ) or introducing a diffuser produced ex situ into the tumorous tissue or the metastasis, illuminating the tumorous tissue or the metastasis through the diffuser, in particular with a specific wavelength activating the photosensitive substance, and thus triggering a chemical reaction, by which the tumorous cells or the metastasis are destroyed. The method steps of "introducing the substance" and of "producing the diffuser" may also take place in reverse order. The illumination does not need to be performed with light in a visible range of wavelengths, the term "illuminate" also incorporates radiation with electromagnetic radiation of other wavelengths, in particular in the range of infrared or ultraviolet.

The step of introducing the photosensitive substance can be carried out by systemic administration of a substance which principally gathers in the tumorous tissue or the metastasis. The substance may also be administered locally to the tumorous tissue or the metastasis. Furthermore, it is possible to release the substance through the diffuser or the diffuser blank.

What is claimed is:

1. A diffuser blank suitable for producing a light diffuser, the diffuser blank comprising a transparent, solid, and thermoplastic diffuser material configured to liquefy at least partly when positioned in a vicinity of a boundary layer of a porous shaping material, wherein the liquefied diffuser material is capable to penetrate into and to re-solidify in pores of the boundary layer of the shaping material, thereby being configured to produce a light scattering surface structure, wherein the porous shaping material has a pore structure and the light scattering surface represents a negative of the pore structure,
  wherein the diffuser blank comprises a proximal end, a distal end, and a longitudinal axis that extends between the proximal end and the distal end,
  wherein the proximal end of the diffuser blank is suitable for coupling light into the diffuser blank or into the diffuser produced therefrom,
  wherein the diffuser blank comprises a proximal region and a distal region, the proximal region having a basic cross-section normal to the longitudinal axis that is constant or decreasing towards the distal end and the distal region having a basic cross-section normal to the longitudinal axis that is constant or decreasing towards the distal end,
  wherein the proximal region comprises a proximal surface region and the distal region comprises a distal surface region,
  wherein the diffuser blank comprises an outer lateral surface, said outer lateral surface comprising the proximal surface region and the distal surface region, wherein the distal surface region comprises protruding energy directors or consists of protruding energy directors, wherein at least part of the diffuser material is positioned or positionable at the distal surface region where the light scattering surface structure is to be produced, said distal surface region being able to be brought into contact with the porous shaping material, and,
  wherein the energy directors are arranged to define points at which the thermoplastic diffuser material liquefies when mechanical vibrations are applied to the diffuser blank.

2. The diffuser blank according to claim 1, wherein the proximal end is further suitable for the mechanical vibrations to be applied to the diffuser blank.

3. The diffuser blank according to claim 1 being pin-shaped.

4. The diffuser blank according to claim 1, wherein, for reflecting light coupled or to be coupled into the diffuser blank or into the diffuser produced therefrom, the diffuser bland comprises further surface areas that are polished or coated.

5. The diffuser blank according to claim 1, wherein the diffuser blank comprises further surface areas situated at least one of near the proximal end of the diffuser bland and in a distal face of the diffuser blank, wherein, for reflecting light coupled or to be coupled into the diffuser blank or into the diffuser produced therefrom, the further surface areas are polished or coated.

6. The diffuser blank according to claim 1, being suitable as an illuminative implant and comprising, as diffuser material, a clinically applicable, thermoplastic polymer.

7. The diffuser blank according to claim 6, wherein the polymer is biologically resorbable.

8. The diffuser blank according to claim 1, and further comprising a diffuser core equipped for further functions, and wherein the diffuser material is situated at the periphery of the diffuser core.

9. The diffuser blank according to claim 1, and, for further scattering light coupled into the diffuser blank or the diffuser produced therefrom further comprising reflecting particles within the diffuser material or within a further transparent material.

10. A diffuser blank suitable for producing a diffuser, the diffuser blank comprising a transparent, solid, and thermoplastic diffuser material configured to liquefy at least partly when positioned in the vicinity of a boundary layer of a porous shaping material, wherein the liquefied diffuser material is capable to penetrate into and to re-solidify in pores of the boundary layer of the shaping material thereby being configured to produce a light scattering surface structure, wherein the porous shaping material has a pore structure and the light scattering surface represents a negative of the pore structure,
  wherein the diffuser blank further comprises a proximal end suitable for coupling light into the diffuser blank or into the diffuser produced therefrom,
  wherein the diffuser blank is further equipped for at least one of reflecting and further scattering the light coupled into the diffuser blank or into the diffuser produced therefrom,
  wherein the diffuser blank comprises a diffuser core that is opaque to the light coupled into the diffuser blank or into the diffuser produced therefrom, and
  wherein the diffuser material is arranged on a periphery of the diffuser core such that the diffuser material is capable to guide light that is coupled into the diffuser blank or into the diffuser produced therefrom from the proximal end towards a distal end of the diffuser blank or the diffuser produced therefrom by reflections on a lateral surface of the core and at least partial reflection on a lateral surface of the diffuser material arranged on the diffuser core periphery.

11. The diffuser blank according to claim 10, wherein, for reflecting the light coupled or to be coupled into the diffuser blank or into the diffuser produced therefrom, the diffuser blank comprises suitably polished or coated surface areas.

12. The diffuser blank according to claim 11, wherein the suitably polished or coated surface areas are surfaces of the diffuser material or of the diffuser core consisting of a further material different from the diffuser material.

13. The diffuser blank according to claim 10, wherein, for reflecting radially outwards the light to be coupled into the diffuser blank or into the diffuser produced therefrom, the proximal end of the diffuser blank comprises a conical light reflecting surface.

14. The diffuser blank according to claim 13, wherein the conical light reflecting surface is arranged in a proximal opening of the core of the diffuser blank.

15. The diffuser blank according to claim 10, wherein, for reflecting the light coupled into the diffuser blank or into the diffuser produced therefrom, at least one of a distal face and a lateral surface near the proximal end are light reflecting surfaces.

16. The diffuser blank according to claim 10, wherein, for further scattering the light coupled into the diffuser blank or the diffuser produced therefrom, the diffuser material or a further transparent material comprised by the diffuser blank contains reflecting particles.

17. The diffuser blank according to claim 10, wherein the thermoplastic diffuser material is liquefiable by a first wavelength, wherein the proximal end is suitable for coupling into the diffuser blank light of the first wavelength for liquefaction of the diffuser material and light of a second wavelength to be scattered by the diffuser produced from the diffuser blank, and wherein the diffuser blank further comprises a material capable of absorbing the light of the first wavelength.

18. The diffuser blank according to claim 1, wherein a length of the diffuser blank is adjusted to a depth of the bone area to be treated, and a length of the distal region is adjusted to a size of the bone area to be treated.

19. The diffuser blank according to claim 10, wherein the diffuser core is equipped for a load bearing function.

20. The diffuser blank according to claim 1, wherein the cross-section of the proximal region is constant and the protruding energy directors protrude beyond the proximal surface region.

21. The diffuser blank according to claim 1, comprising a distal end region that is blunt and formed by a lateral outer surface distally of the distal surface region, wherein the protruding energy directors protrude beyond the lateral outer surface forming the blunt distal end region, or wherein the distal end region is pointed and formed by a lateral outer surface distally of the distal surface region, wherein the protruding energy directors protrude beyond the lateral outer surface forming the pointed distal end region.

* * * * *